United States Patent [19]

Mitch

[11] 4,058,628
[45] Nov. 15, 1977

[54] DISINFECTANT COMPOSITION COMPRISING PINANOL

[75] Inventor: Frank A. Mitch, Jacksonville, Fla.

[73] Assignee: SCM Corporation, New York, N.Y.

[21] Appl. No.: 728,259

[22] Filed: Sept. 30, 1976

[51] Int. Cl.$^2$ .................... A01N 9/24; A61L 13/00
[52] U.S. Cl. .................................................. 424/343
[58] Field of Search ................ 424/343; 260/631.5

[56] References Cited

U.S. PATENT DOCUMENTS 3,723,542   3/1973   Risco et al. .................. 260/631 B

*Primary Examiner*—Leonard Schenkman
*Attorney, Agent, or Firm*—Jerry K. Mueller, Jr.

[57] ABSTRACT

A disinfectant composition comprises a germicidally effective amount of pinanol dispersed in a fugitive carrier, preferably water.

7 Claims, No Drawings

DISINFECTANT COMPOSITION COMPRISING PINANOL

BACKGROUND OF THE INVENTION

The present invention relates to a pinanol and more particularly to its use in a disinfectant composition.

Heretofore, the terpene alcohol pinanol has been used predominantly as an intermediate in synthesis of terpene chemicals and sparingly as a final product. For example, it is well known that linalool (an especially valuable essence for perfumes) can be synthesized using 2-pinanol as an intermediate during the synthesis (eg. British Patent No. 953,500). Typically the 2-pinanol itself is derived by catalytically hydrogenating pinane hydroperoxide with a nickel chrome catalyst (Russian Patent No. 340,648), by oxidizing pinane with a base such as sodium hydroxide (U.S. Pat. No. 3,723,542), or by various other techniques well known in the art.

It now has been discovered that a highly effective disinfectant composition can be made from pinanol.

SUMMARY OF THE INVENTION

The present invention is a disinfectant composition comprising a germicidally effective amount of pinanol dispersed in a fugative carrier. Preferably the pinanol is 2-pinanol and the carrier is water.

DETAILED DESCRIPTION OF THE INVENTION

Pinanol is a bicyclic terpene alcohol. The preferred pinanol of this invention is the tertiary alcohol 2-pinanol (2,6,6-trimethyl-bicyclo (3.1.1)-heptan-2-ol). It is conceivable that various of the hydrogens could be substituted by alkyl, halogen, nitrile, and the like, i.e., having the hydroxylated carbon nucleus or skeleton of a pinanol. It also is conceivable that some unsaturation could be present. The present invention will be described in detail with 2-pinanol, though such is merely descriptive and not limitative of the present invention.

The pinanol is dispersed in a fugative carrier for compounding the disinfectant composition of this invention. While the carrier can be an organic solvent, it is preferred to use water as the carrier. The carrier should be fugative preferably at about room temperature leaving no residue or at best an innocuous residue. Also, the carrier should not diminish the disinfectant qualities of the pinanol. Pinanol can be emulsified or dispersed in water conventionally with the aid of an emulsifier, dispersant, surfactant or the like. Preferably, the pinanol is emulsified in water with a soap. For efficiency and economy the soap is derived from terpene chemical operations as is the pinanol. Suitable soaps can be derived from rosin acids, fatty acids and mixtures thereof by their reaction with, for example, alkali metal or alkaline earth metal.

At high concentrations of pinanol in the disinfectant composition (roughly around 80 weight percent), the pinanol can tend to crystallize from the water upon standing for extending periods of time. The pinanol can be re-dispersed by mild heating or by the addition of a clarifying agent such as an alcohol. Such alcohols include, for example, isopropanol, ethanol, primary alkanols of six to sixteen carbon atoms and various other alcohols. Such alcohols also can enhance the germicidal activity of the pinanol. Typically, from about 3 to about 12 weight percent of the alcohol is sufficient to suppress crystal formation. Alternatively, the concentration of pinanol can be decreased or the proportion of soap increased in order to prevent crystallization of the pinanol in water. The disinfectant composition also can contain odorants (eg. dipentene) to impart an odor conducive to user acceptance or can be colored for special asthetic appeal.

The particular isomeric form of the 2-pinanol is not limitative in its effectiveness as a disinfectant. The proportion of cis-, and trans-2-pinanol can be typical of that normally obtained during production of the pinanol (generally a cis:trans ratio of from about 3.5:1 to 3.8:1), or such proportions can be adjusted to any convenient value that is necessary or desirable including all cis-, or all transpinanol.

The effectiveness or germicidal activity of the pinanol disinfectant composition is determined by accepted methods of the art. Such methods include the AOAC phenol coefficient method and the AOAC use-dilution method of the Association of Official Analytical Chemists as found in their publication *Methods of Analysis*, AOAC 12th Edition, 1975, the same incorporated herein by reference. Generally, the present disinfectant composition is classified as a "janitorial or household" disinfectant effective against enteric organisms rather than a "medical or surgical" disinfectant also effective against pyogenic organisms (such as staphylococcus aureus). Further, details on this can be found in *Kirk-Othmer Encyclopedia of Chemical Technology*, 2nd Edition, Volume 2, pages 604/648 (Interscience Publishers, New York, New York 1964), the same expressly incorporated herein by reference.

Pinanol also can be used as disinfectant additive to enhance or augment the germicidal activity of other disinfectants such as, for example, pine oil or the like. Pine oil generally contains 50-60% alpha-terpineol with lesser amounts of terpene hydrocarbons, borneol, fenchyl alcohol, related terpineols, terpene ethers, terpene ketones and terpene phenols. The proportion of pinanol in the disinfectant composition (or to be used as an additive) is related to the particular use intended therefor and the particular organisms sought to be eliminated. Typically, as little as about 10% by weight of 2-pinanol can enhance germicidal activity when used as an additive. A pinanol disinfectant composition can contain up to about 80% pinanol by weight or higher depending upon, among other factors, how well the pinanol can be emulsified and stabilized in water.

The following examples show in detail how the present invention can be practiced, but they should not be construed as limiting the present invention.

EXAMPLE I

A 2-pinanol disinfectant composition was subjected to the AOAC phenol coefficient method in order to determine its germicidal effectiveness against salmonella typhi (*Methods of Analysis*, Association of Official Analytical Chemists, p. 57, 12th Edition, 1975).

The disinfectant composition had the following composition by weight percent:

| | |
|---|---|
| 2-pinanol (cis:trans ratio 5:1) | 80.0 |
| *SYLVATAL 40 | 9.0 |
| KOH (50% aqueous solution) | 3.4 |
| Water | 7.6 |

*SYLVATAL is registered trademark of Sylvachem Corporation, Jacksonville, Florida, and SYLVATAL 40 is a distilled tall oil consisting of about 70% tall oil fatty acids and about 30% tall oil rosin acids.

The phenol coefficient was determined to be 8.0. A commercial pine oil composition also was tested and found to have a phenol coefficient of only 6.5. These results clearly demonstrate the superior germicidal activity of the 2-pinanol disinfectant composition.

EXAMPLE II

The 2-pinanol used in these examples is made by hydrogenating pinane hydroperoxide and is recovered therefrom by conventional distillation techniques. Pinanol bottoms is the fraction of higher boiling constituents remaining from the hydrogenation-distillation operation. The pinanol bottoms contains a large proportion of $\alpha$-terpineol which is the chief component of pine oil. The pinanol bottoms were formulated into a disinfectant composition and the phenol coefficient thereof determined.

Pinanol bottoms have the following composition by weight percent:

| | |
|---|---|
| $\alpha$-terpineol | 78.8 |
| 2-pinanol | 13.8 |
| linalool | 1.2 |
| related alcohols | 6.2 |

The pinanol bottoms disinfectant composition by weight percent is as follows:

| | |
|---|---|
| Pinanol bottoms | 80.0 |
| SYLVATAL 40 | 9.0 |
| KOH (50% aqueous solution) | 3.4 |
| Water | 7.6 |

The phenol coefficient of this disinfectant composition was determined to be 7.0. Thus, the 2-pinanol is effective as an additive to enhance the germicidal activity of conventional disinfectant compositions.

EXAMPLE III

The pinanol disinfectant composition of Example I was subjected to the use-dilution method in order to determine its germicidal activity against salmonella choleraesuis (*Methods of Analysis,* Association of Official Analytical Chemists, p. 59, 12th Edition, 1975).

A use-dilution of 1:128 was found for the pinanol composition. A commercial pine oil was found to have a 1:112 use-dilution. Economic and time factors restricted further use-dilution tests; however, based on the significant phenol coefficient results reported in Example I, it is believed that a much higher use-dilution number could be displayed by the present pinanol disinfectant composition. These results, though, do demonstrate the superiority of the present pinanol composition over conventional pine oil.

EXAMPLE IV

Several more 2-pinanol disinfectant compositions were formulated and their stability as measured by crystal formation evaluated. In none of the following formulations did any crystals develop after extended periods of storage. The following pinanol disinfectant compositions are given by weight percent.

| | A | B | C | D |
|---|---|---|---|---|
| 2-pinanol | 64.0 | 50.0 | 25.0 | 73.0 |
| SYLVATAL 40 | 9.0 | 12.5 | 9.0 | 9.0 |
| KOH (50% aqueous solution) | 3.4 | 4.8 | 3.4 | 3.4 |
| Dipentene | 16.0 | — | — | — |
| Isopropanol | 16.0 | — | 7.0 | 7.0 |
| Water | 7.6 | 32.7 | 55.6 | 7.6 |

The foregoing compositions display representative formulations of the pinanol disinfectant composition of the present invention.

I claim:

1. A disinfectant composition for inhibiting enteric microorganisms comprising:
   a germicidally effecive amount of pinanol;
   a soap; and
   an aqueous carrier, said soap being in a proportion for providing a stable aqueous dispersion of said pinanol in said aqueous carrier.

2. The disinfectant composition of claim 1 wherein said soap is an alkali metal or alkaline earth metal salt of a rosin acid, a fatty acid, or mixtures of said acids.

3. The disinfectant composition of claim 1 wherein said pinanol is 2-pinanol.

4. A method for inhibiting enteric microorganisms which comprises applying thereto a disinfectant composition comprising a germicidally effective amount of pinanol stably dispersed in an aqueous carrier.

5. The method of claim 4 wherein said pinanol is 2-pinanol.

6. The method of claim 4 wherein said pinanol is stably dispersed in said aqueous carrier with the aid of a soap.

7. The method of claim 6 wherein said soap is an alkali metal or alkaline earth metal salt of a rosin acid, a fatty acid, or mixtures of said acids.

* * * * *